United States Patent [19]
Shimoni et al.

[11] Patent Number: 4,930,508
[45] Date of Patent: Jun. 5, 1990

[54] REDUCING RESPIRATORY MOTION ARTIFACTS IN NUCLEAR MAGNETIC RESONANCE IMAGES

[76] Inventors: Yair Shimoni; Bilha Nissenson, both of c/o Elscint Ltd., P.O.B. 550, Haifa, Israel, 31004

[21] Appl. No.: 177,699

[22] Filed: Apr. 5, 1988

[30] Foreign Application Priority Data

Apr. 10, 1987 [IL] Israel .................................. 82184

[51] Int. Cl.⁵ .............................................. A61B 5/05
[52] U.S. Cl. ................................ 128/653 A; 128/716
[58] Field of Search .................... 128/653 A, 716, 653; 324/307, 309

[56] References Cited

U.S. PATENT DOCUMENTS

| | | | |
|---|---|---|---|
| 4,564,017 | 1/1986 | Glover | 128/653 |
| 4,567,893 | 2/1986 | Charles et al. | 128/653 |
| 4,614,195 | 9/1986 | Bottomley et al. | 128/653 |
| 4,663,591 | 5/1987 | Pelc et al. | 128/653 |
| 4,720,678 | 1/1988 | Glover et al. | 324/309 |
| 4,730,620 | 3/1988 | Bailes | 128/653 |

OTHER PUBLICATIONS

"Respiratorily Ordered Phase Encoding (ROPE): A Method for Reducing Motion Artifacts in MR Imaging", by D. R. Bailes et al., pp. 835–838, Journal of Computer Assisted Tomography, vol. 9 (4) Jul./Aug. 1985.

*Primary Examiner*—Kyle L. Howell
*Assistant Examiner*—John D. Zele
*Attorney, Agent, or Firm*—Sandler, Greenblum and Bernstein

[57] ABSTRACT

A reordering system for reducing respiratory artifacts in magnetic resonance images. The respiration cycle of the patient is measured and divided into N exclusive intervals. A different encoding amplitude is assigned to each interval in a first look-up table (LUT). The encoding pulses are selected by the first LUT responsive to measured respitory intervals. After M encoding pulses have been selected, a new LUT is constructed from the unused encoding pulse amplitudes using a new number (N–M) intervals. The new LUT is then used for another given number of encoding pulses. Other new LUT's are constructed after given numbers of encoding pulses are used until all encoding pulses are used.

14 Claims, 3 Drawing Sheets

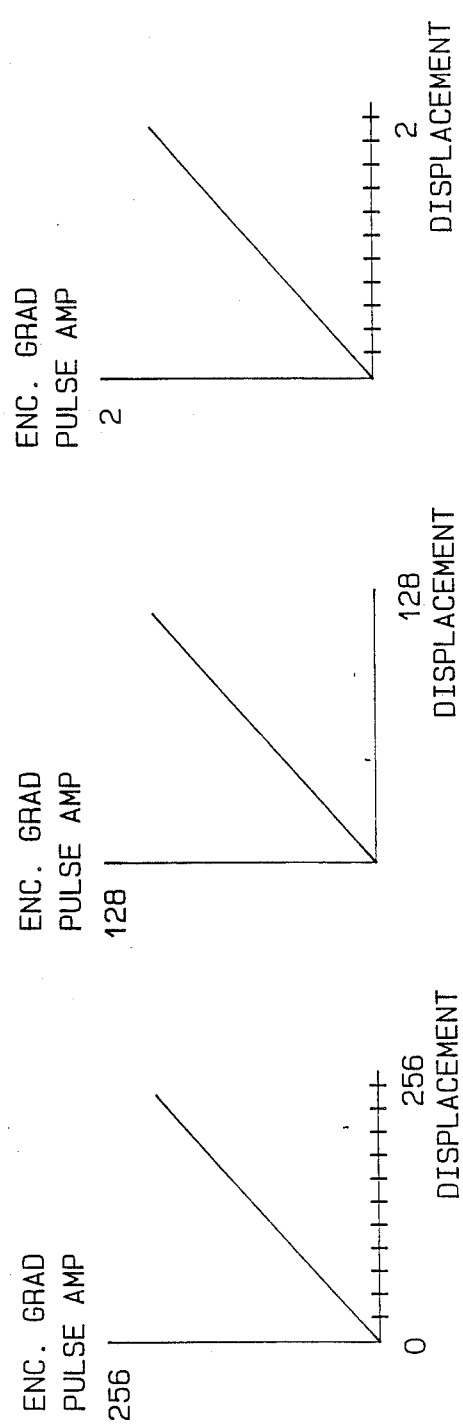

REDUCING RESPIRATORY MOTION ARTIFACTS IN NUCLEAR MAGNETIC RESONANCE IMAGES

FIELD OF THE INVENTION

This invention is concerned with Nuclear Magnetic Resonance (NMR) imaging methods and apparatus; and more particularly with methods and apparatus for reducing respiratory motion artifacts in NMR images.

BACKGROUND OF THE INVENTION

One of the major problems presently encountered by users of NMR imaging equipment is the motion artifacts, particularly in the images of the upper thorax and the abdomen and a reduction of the motion artifacts is a goal of suppliers of the NMR imaging equipment. A primary cause of the motion artifacts is breathing. Breathing introduces quasi-cyclic changes in the RF data signals received by the NMR system's receiver. This "foreign" frequency causes a number of copies of the images, called "shadows" to appear along the encoding axis, blurring the image and causing artifacts. As these quasi-cyclic changes result from non-linear motions along all three axes, to date no software post-acquisition processing method has been discovered that is effective in correcting the resulting artifacts.

The prior art reveals numerous approaches and methods which have been tried in attempts to minimize the artifacts caused by the breathing of the subject during the NMR imaging scan process. For example, post acquisition data processing methods have been tried to reduce the artifacts. This approach however in addition to the aforementioned problem of three dimensional motion, inherently requires significantly more time per patient. The time is required for the post-acquisition processing of the data.

See for example the technical note entitled "Respiratorily Ordered Phase Encoding (ROPE): A Method for Reducing Motion Artifacts in MR Imaging" by D. R. Bailes et al pp 835–838, Journal of Computer Assisted Tomography, Vol. 9 (4) Jul./Aug. 1985; U.S. Pat. Nos. 4,564,017 and 4,567,893.

In the past, those skilled in the art attempted to minimize the motion artifacts caused by breathing by various breathing gating schemes. A serious drawback in the use of gating schemes, among other things, is that respiratory gating requires additional sophisticated and expensive equipment to generate gating signals and also requires appreciably longer data acquisition time periods with consequent reduced throughput. Since, "throughput" is a key requirement of any NMR system, scientists in the field are continually seeking to shorten the time required for the examination using "gating" or to find faster alternatives to such time intensive prior art processes.

Gating comprises waiting with the pulse train until the selected thoracic position occurs. This means that there is no exact repetition time TR but rather the repetition is controlled by the breathing. Gating thus limits the user, as TR is an important factor affecting image quality. Its control is usually left to the user as a tool in selecting the type of contrast. In gating, TR is a few seconds, instead of the usual TR time of under a second, causing the gated study to last much longer then a non-gated one.

More recently methods have been tried which allow the user to fix TR, but couple the encoding pulse's amplitude to the thoracic position, instead of linearly increasing the amplitude at each pulse repetition, as is the usual procedure. A popular method makes the encoding amplitude a monotonic function of the thoracic position. Thus, after reordering the pulses according to the encoding pulse amplitude, most of the effects of the breathing frequency are eliminated.

Another approach is to use the parity of repetition (whether it is an odd or even one) to select the encoding amplitude. The parity scheme creates shadows (artifacts) that occur a half-image away.

Making the encoding pulse amplitude a simple (linear, say) function of the thoracic position introduces new problems. Some positions are more likely than others and will probably repeat before the less likely positions occur the first time. This "wastes" time, whatever is done with the redundant data obtained because of the repetitions (the redundant data can be discarded, averaged with the previous data from the same amplitude, etc.).

Since the repetition time and the breathing frequency are not synchronized some breathing cycle positions will occur a second or a third time (hereinafter called "double sampling") before others have occurred once. That happens because the breathing cycle position is "random" relative to the occurrence of the encoding pulses and also because during the breathing cycle there are sections with relatively slow motion and others with relatively fast motion. The position axis values sensed during the parts of the cycle where the motion is slow are more likely to be detected in a random sampling arrangement than the position axis values where the motion is fast, partially because the slower motion part of the breathing cycle extends over a longer time period.

Using the integral of the temporal probability function of the thoracic position as the mapping function from position to encoding pulse amplitude creates a flat, nearly constant, probability function for the encoding amplitudes (the method is known as "Histogram Equalization"). However, as the thoracic position is a function of the breathing process and is independent of TR, the position is random relative to the pulse train number. The statistical nature of the sampling will therefore still cause some positions to repeat before others occur even once. Thus, this solution is also not efficient enough.

In one particular prior art method used to speed up the process of activating all of the required encoding pulses, the encoding pulse amplitudes per pulse repetition are selected by using "bins" instead of varying the amplitude of each ensuing encoding pulse as a direct function of the thoracic or breathing cycle position. Each bin is defined by a range of breathing or respiratory cycle positions. A range of encoding pulse amplitudes is assigned to each bin. Each received breathing cycle position then determines a bin and the next encoding pulse amplitude is selected from the determined bin.

There may be different methods of selecting the encoding pulse amplitude once the bin is selected. For example, the central amplitude allocated to the bin may be the first amplitude selected when the breathing cycle position first indicates a particular bin. At the second indication of the particular bin, the first amplitude greater than the central amplitude is selected. The third indication of the particular bin selects the encoding pulse amplitude immediately less than the central amplitude. This process continues until all of the encoding pulse amplitudes assigned to the particular bin are used.

The simple bin methods may also increase the data acquisition time. Examine, e.g., the bin method where each bin includes only one encoding amplitude. If a breathing cycle position is sampled which has already been used, the immediate reaction is to skip it. A few sequences of the data could perhaps be skipped without serious loss. However, as more and more encoding amplitudes are used it becomes increasingly more probable that the next sampled position of the breathing cycle will be a double sampling. The probability of sampling a previously unsampled breathing position decreases with time both because less unsampled positions are left and because the more probable positions are usually sampled earlier. The last few encoding amplitudes may therefore require a large number of "aborted" samplings and a very long marginal time to obtain. Larger bins alleviate the problem but do not eliminate it.

The use of different more complicated binning methods may decrease the acquisition time but only partially solves the problem of the artifacts. First of all, the sampling of the breathing cycle position, is random relative to the pulse time. Therefore, one of the bins still will be used up first. The usual case is that this bin has a higher probability of utilization and therefore will be needed again. Thus, a breathing cycle position connected with this bin will be sampled again before the scan period is over with the consequent waste of time.

A further fault of binning is that a step like correction occurs which sets up a series of stepped blocks. These blocks contain "hidden" cyclic components that result in residual shadows. Another relevant problem is the fact that the same breathing cycle position is found twice (inhalation and exhalation) during each breathing cycle except for the extremes, of course. Where more than one slice is required then the other slices will be split into two phases differing by the slice time difference (STD) x(n−1) where n is the number of the slice. The second slice will be phase split by a single STD. The eighth slice will be split by 7 STD's. Since, the STD is in the order of 100 milliseconds, this phase split will cause a noticeable foreign frequency, the amplitude of which approaches that of the breathing motion even for the third slice. This foreign frequency of course results in blurring.

Yet another problem with the binning solution is that it assumes a constant unchanging breathing cycle. In practice breathing cycles tend to vary in amplitude, time and shape. For example the amplitude may decrease thereby eliminating the sampling of certain positions and raising the possibility of corresponding bins not being used entirely or only being partially used. Attempted solutions to these problems raised by varying breathing cycles include limiting the transformation function to a region smaller than that indicated by the breathing amplitude and/or using bins of equal probability rather than bins of equal intervals.

Limiting the transformation function to a region smaller than the breathing cycle tends to waste part of the breathing cycle. Using bins of equal probability suffers because breathing cycle position probabilities also change with variations in the breathing cycle, and the bin borders are then no longer optimal.

The presently available "binning" methods for synchronizing the breathing position and the encoding pulse amplitude also inherently increase the noise regardless of the method used for selecting pulse amplitudes within the bins. The randomness of the breathing position relative to time carries noise in the breathing position axis and in the encoding amplitude axis of the transformation function. Where the samples or the encoding amplitudes obtained by the samplings are spread with a uniform probability over the appropriate interval, the RMS noise will be plus or minus the square root of 1/12 of the bin interval or the size of the amplitudes range associated with the bin. The noise reduces the signal-to-noise ratio, smears the image and has hidden frequencies which may appear as shadows.

BRIEF DESCRIPTION OF THE INVENTION

Accordingly, it is an object of this invention to provide apparatus and processes for overcoming or reducing breathing artifacts obtained during NMR imaging of patients.

More particularly a method of reducing motion artifacts in NMR images is provided using detected respiration cycle parameters to determine the next encoding cycle amplitude to be used in image data acquisition scans, said method comprising the steps of:
(a) determining the amplitude and time parameters of the respiration cycle of a subject to be scanned,
(b) dividing the respiration cycle amplitude into N exclusive intervals,
(c) assigning one of a plurality of different encoding cycle amplitudes in a first look up table [LUT] to each of the N intervals to select said encoding cycle amplitude,
(d) using encoding pulse amplitudes to encode locations of received signals selected by said first LUT responsive to sampled respiration cycle amplitudes,
(e) changing the LUT after providing a number M of encoding pulses,
the step of changing the LUT comprises the steps of:
(f) using a new number (N-M) of intervals and only the unused N-M encoding cycle amplitudes in the changed LUT to obtain further encoding cycle amplitudes, and
(g) repeating step (e) until there is data for each wave number or view number, whereby an image can be reconstructed with minimized motion artifacts.

An additional feature of the present invention is that the breathing cycle parameters are continuously determined or rechecked and at the time of changing the LUT, new up-to-date data obtained from the rechecking of the breathing cycle is used for the new LUT.

Still another feature of the inventions utilizes a variable number M in step (e) when it is repeated according to step (g).

A further feature of the present invention is the use of the direction of the thoracic motion as an additional parameter (for example as a sign tagged onto the position) in creating the LUT.

A further feature of the invention is replacing the LUT by a circuit which calculates the encoding pulse amplitude for each sampling of thoracic position.

A still further feature of the invention is replacing the LUT by a computer routine (a subroutine) which calculates said encoding amplitude on a general purpose (or a multipurpose) processor.

Another feature of the invention comprises using an approximate relation between encoding amplitude and thoracic position, based on an approximate probability, based in turn on an approximate cycle shape.

An additional feature of the invention comprises limiting the size of change from the original LUT or function and allowing a few cases of "wastage".

BRIEF DESCRIPTION OF THE DRAWING

The above named and other features and objects of the present invention believed to be novel are set forth with particularity in the appended claims; while the invention itself will be best understood along with the advantages thereof by referring to the following description, taken in conjunction with the accompaning drawings, in which:

FIGS. 2a, 2b, and 2c shows examples of various look up table sequences useful in one embodiment of the invention;

GENERAL DESCRIPTION

Figure 1:
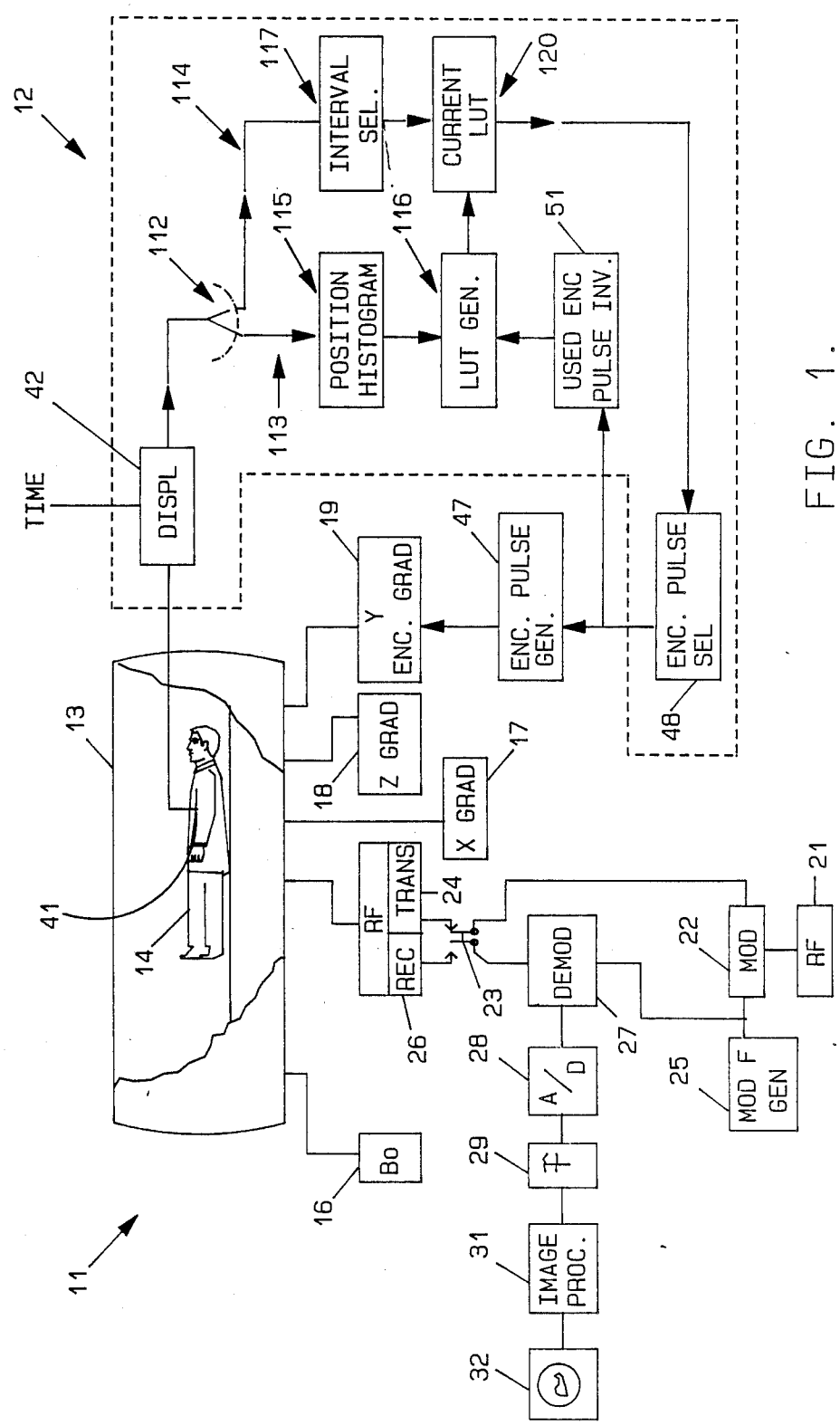
FIG. 1 depicts in block diagram form the inventive system.

A system 11 for obtaining NMR imaging data, as shown in FIG. 1, includes an arrangement for minimizing or reducing motion artifacts, generally indicated at 12. The general system 11 includes a large magnet 13 for creating a large static magnetic field into which a patient 14 is placed. To obtain the image data, a large static magnetic field is generated by magnetic generator 16 indicated at block Bo. The large static magnetic field causes certain nuclei or "spins" to align with the field. Orthogonal gradients are used to locate the source of what are referred to as free induction decay (FID) data signals received from the patient. The gradients are generated by the X gradient generator 17 the Z gradient generator 18 and the Y gradient generator 19. The large static magnetic field is in the Z direction.

As is well known, to obtain the FID signals it is necessary to "tip" the spins from the normal position of alignment with the large static magnetic field in the Z direction to a position having at least a projection in the XY plane. Radio frequency RF pulses having a desired frequency (known as the Larmor frequency) are used to tip the spins. The RF pulses are transmitted through the RF probes or coils (not shown) used in the system. An RF generator 21 generates the radio frequency pulse which may be modulated by modulator 22 and is switched by switch 23 to the transmitter 24 for connection to an RF transmitting coil not shown.

In the normal mode of operation the Z gradient is used as the plane selecting gradient; that is, the RF pulse is applied during the application of the Z gradient. The signals which are received after the RF pulse has been terminated are detected by either the same coils used for transmitting or by separate receiving coils. In either case the coil is attached to a receiver 26. The received signal is connected by the switch 23 to a demodulator 27. Note that the modulator 22 and the demodulator 27 receive their modulating frequency from modulating frequency generator 25. The demodulated received signal is then converted from analog to digital signals in the analog to digital converter 28. The digital signals are then operated on and transferred from the time domain to the frequency domain by the Fourier operator 29. The frequency domain digital signals are then processed in the image processor 31 to provide an image for display unit 32.

The X gradient is used as a view gradient; that is in a preferred embodiment, it is applied during the receipt of the signals obtained in response to an echo signal providing scan sequence.

The image processor processes the received signals so that a pixel value is provided for each pixel in the image. For example, in the usual case, the image is made up of 256×256 pixels arranged in X columns and Y rows. The pixel values are obtained after a Fourier transform of the data received. The data is comprised of wave number or view number related amplitudes where the pertinent X data number is generated as a function of time over the X gradient and the Y wave number is generated by integrating the Y gradients over time. The Y gradients are proportional to the "encoding pulse" amplitudes in other words the length of the encoding pulses are kept constant.

The values of the encoding pulse amplitudes used are selected to minimize motion artifacts caused, for example, by the patient's breathing. It is recognized that the motion artifacts are most problematical in the Y encoding direction because there is a larger time period between changing the vertical (Y) wave numbers, i.e. the phase encoding pulse amplitudes, as compared to changing the horizontal (X) pulse amplitudes or wave numbers. In other words Y (encoding) wave numbers are changed less frequently (once per repetition time span) than X (viewing) wave numbers which are usually changed many times for each echo signal received. The Y encoding gradient and consequently the Y wave number changes once per repetition of the scan.

Means including sensor 41 are provided for measuring the displacement versus time caused by the patient's breathing. After a "learning period" the displacement characteristic is transformed into a position histogram which is then divided into intervals. Phase encoding pulse amplitudes are assigned to the interval, one encoding amplitude per interval. The interval sizes, may be selected so that, based on the learning period, each encoding amplitude has the same probability of being used as any other amplitude.

The sensor means 41 which is part of the arrangement for reducing motion artifacts is used for determining the position of patient's chest during the breathing cycle. Unit 42, also included in arrangement 12, associates the displacement with time.

The output of the sensor means 41 is translated by displacement circuit 42 into numbers indicating where in the respiratory displacement cycle the parts of the patient are at a particular measuring time. It is the respiratory motion of the parts of the patients body that causes artifacts.

Switch 112, in one embodiment shown in FIG. 1, switches between "learning" mode 113 used prior to the NMR study and "examination" mode 114 used during the study. In the learning mode the displacement data is sampled at equal intervals, the resuls are collected and a position histogram is created in Position Histogram unit 115. The Position Histogram is fed into LUT generator 116 to form an appropriate LUT that transforms chest positions to encoding pulse amplitudes. The LUT is fed into current LUT unit 120. The first LUT attempts to follow a linear mapping function (i.e. a transformation from thoracic position to encoding pulse amplitudes such that a reordered representation of the pulse amplitudes by increasing size will prove linear and not include "hidden" frequencies). Other first LUTs may be used but an LUT that follows a linear mapping function is preferrable.

During the actual study the system is switched to examination mode 114, the sampled breathing position is input to interval selector 117, where the interval that includes the sampled position is determined. This interval is transformed by Current LUT unit 120 to an encoding pulse amplitude. This is done via encoding pulse selector 48, which causes Encoding Pulse Generator 47 to generate an appropriately sized encoding pulse for the next sequence. At the same time the encoding pulse is fed into used Encoding Pulse Inventory unit 51 which after receiving a preset number of pulses resets the LUT generator 116 to cause a new LUT to be generated. The new LUT takes into account the new number of available pulses and their sizes. The new LUT becomes the current LUT unit 120 for use with the next sampled breathing position. This continues until no unused encoding pulse amplitudes are left.

Different embodiments of this system have slightly different features. In one version, the position histogram is updated continuously using the last N positions sampled. The updated histogram is fed into LUT generator 120 so that each time a new LUT is generated, it is based on an updated histogram.

In another and non-linear version of the system where both the intervals and the locations of the encoding pulse amplitudes are changed the LUT generator 116 is limited so that it cannot move an encoding pulse amplitude more than a predetermined distance p from its original position in the first LUT of a study. This limitation may cause some amplitude intervals not to be included in the LUT. If a further sampled position points to one of these not included intervals then the sample is "wasted" (it may be discarded or the sampled position may be used to select the same encoding pulse amplitude as previously, or any other solution, but the sample is "wasted" in terms of study duration). Thus, the study length may be slightly increased relative to the minimum possible, however the image error previously encountered due to a linear mapping function is reduced.

A different version of the system replaces the LUT by a circuit which calculates the encoding pulse amplitude for each sampled position.

Another version of the system replaces the LUT by a program residing in a digital processor which calculates the encoding amplitude for the sampled position.

Yet another version teaches storing the inputs to all LUTs to be used, i.e. the position intervals for each LUT to be used during the study. Then, generating a new LUT is done by just assigning encoding pulse amplitudes to the position intervals.

A feature of another version is that the breathing cycle shape or the histogram used may have an analytical shape allowing the generation of new LUTs by LUT generator 116 by changing only a few parameters, one of which is the number of remaining pulses.

In a specific example the motion is assumed to be sinusoidal:

$$P = A(1 - \cos[w(t - to)]) \quad (1)$$

where:
P is the thoracic position and ranges from 0.0 to 2A,
A is the amplitude,
W is the angular velocity,
t is the elapsed time, and to is a time when the thoracic position is exactly at minimum (P=0).

Equal probability intervals are then given by $$\delta t(j) \leq \delta t \leq T/N \quad (2)$$

where:
T is the breathing period $T = 2\pi/W$, and
N is the number of intervals or in this case number of unused encoding pule amplitudes, and
t(j) is the jth interval, which equals any interval $\delta t$.

Thus, the interval in which a sampled position is located is given by $$j = 1 + [N \arccos(1 - P/A)/\pi] \quad (3)$$

where:
P is the sampled position,
[ ] the square brackets denote the integer part of the enclosed expressions value,
arc cos is the inverse of the cosine function which ranges from 0 to $\pi$, and
j is the ordinal number of the interval, or the ordinal number of encoding pulse to be used.

It is evident that for this assumption updating the LUT (or function) is extremely easy—just change N (and A if the histogram is continuously updated). This is simple enough for real-time updating after each pulse.

An important operation of the system is that the LUT selector selects another LUT which provides larger displacement intervals stocked with previously unused amplitudes. The use of larger intervals is shown, for example, in FIG. 2 which shows a first LUT FIG. 2a indicated by the graph having intervals along the abscissa and encoding pulse strengths or amplitudes along the ordinate. In the graph representing the first look up table 2a the total respiratory displacement is divided, into 256 intervals. Each of the 256 intervals is assigned one encoding pulse amplitude. Thus, whenever a displacement interval is selected in accordance with the measured displacement, a particular encoding pulse is also selected from the LUT.

Assume that half of the intervals have been selected and used, then a new LUT having only 128 intervals is selected as shown in FIG. 2b. Here again the respiratory intervals are shown on the abscissa and the encoding pulse amplitudes are shown on the ordinate. The encoding pulse amplitudes are selected using this LUT until for example half of the 128 intervals are used, then another LUT is selected having 64 intervals, etc. This process continues until in the next to the last LUT there are only two intervals as shown in FIG. 2C. Then whatever displacement is detected one of the two intervals is selected which in turn selects an encoding pulse amplitude. The next interval is the entire respiratory displacement and the remaining encoding pulse amplitude that has not yet been used is selected regardless of the respiratory displacement.

Figure 3:
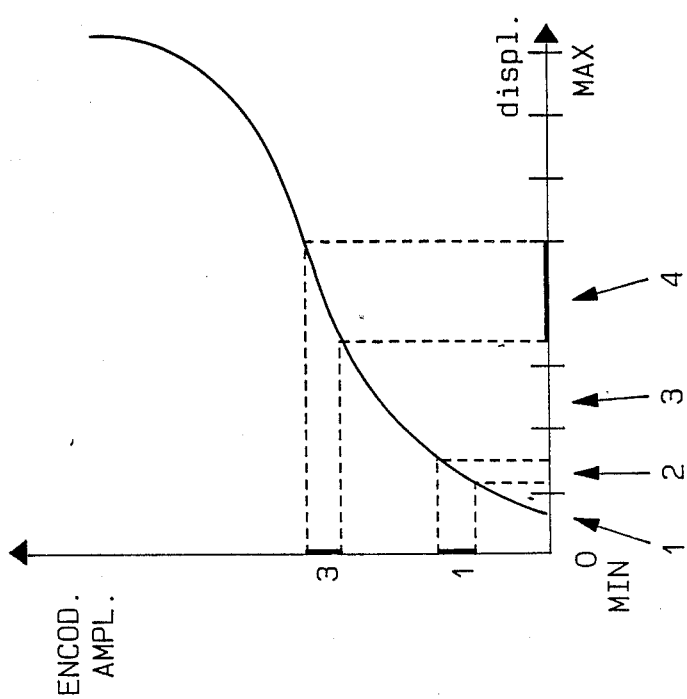
FIG. 3 shows look up tables of another embodiment.

FIG. 3 shows an alternative method whereby the intervals are varied as an inverse function of the probability of occurrence. Thus the maximum and minimum displacements that are at the end of inhalation and the end of exhalation are assigned to the shortest displacement intervals since at the maximum and minimum displacements the motions are slowest. The slow motion results in the chest remaining in those positions for longer periods of time making the probabilities of sampling an extreme displacement greater than average.

This is reflected in the steeper slope of the integrated probability function near the extreme points as shown in FIG. 3. Using this integrated function as the mapping function results in unequal displacement intervals being needed in order to produce equal encoding gradient amplitude pulse intervals. Thus, in order to obtain the equal phase encoding pulse amplitude intervals 1 and 3, a short displacement interval 2 is needed near the minimum displacement and a longer displacement interval 4 is needed at the middle section, where the motion is faster. This well known method of histogram equalization results in equal probabilities for the different intervals, and helps in selecting all of the encoding pulse amplitudes in a relatively short time period.

Figure 4:
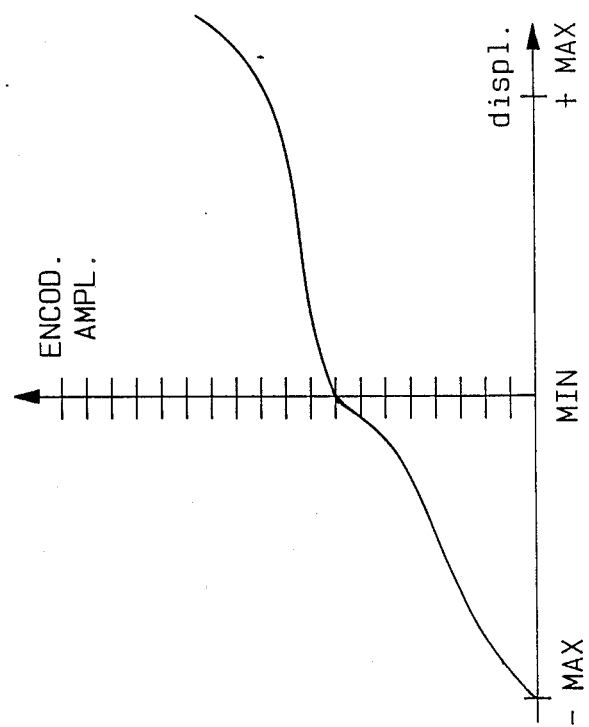
FIG. 4 shows look up tables of yet another embodiment.

The graph of FIG. 4 is a special case wherein the direction of the displacement motion is also measured. Each direction is assigned a sign, say plus for inhalation and minus for exhalation. This sign is tagged onto the displacement so that the range of displacement goes from a minus maximum to a plus maximum. This method enables several slices to be imaged in one scan as now the interslice delay will cause only a phase delay with no phase splitting. Since the direction of motion is taken into account, the delay will always cause a similar change of displacement between the images of two slices at similar positions in the breathing cycle. This method enables several slices to be imaged in one scan as now the interslice delay will cause a phase delay with no phase splitting.

The shape of the curve of FIG. 4 can be derived during the "learning" period, by;

(1) having the system differentiate between "positive" and "negative" displacements and build a separate curve for each such displacement; or (2) just measuring the displacement and reflecting it around the 0 displacement point.

Thus, the intervals are changed either by changing the LUT's on a periodic basis or by changing the size of intervals after each encoding pulse to increase the probability that each encoding pulse is selected once prior to other encoding pulses being selected a multiplicity of times. This method is a preferred method when several slices are to be imaged in one scan as now the interslice delay will cause a phase delay with no phase splitting.

In operation the motion artifacts are minimized by assuring that the encoding pulse amplitudes are selected by the position of the respiration cycle at the time the encoding pulse is used. This enables the minimization of errors and motion artifacts without increasing the data acquisition time.

While the invention has been described with reference to particular embodiments, it should be understood that these embodiments are described by way of example only and not as limitations on the scope of the invention. Accordingly it should be understood that within the scope of the appended claims, the invention may be practiced otherwise than as specifically described.

What is claimed is:

1. A method of reducing respiratory motion artifacts in NMR images, said method comprising the steps of:
   (a) prior to scanning determining an average respiration cycle of a subject to be scanned in a magnetic resonance scanning system,
   (b) dividing the average respiration cycle into a number of intervals,
   (c) assigning at least one phase encoding pulse characteristic to each of the intervals, each assigned phase encoding pulse with a different characteristic determining a different phase,
   (d) scanning the subject,
   (e) measuring thorax displacement values of the respiration cycle of the subject while scanning the subject,
   (f) selecting an interval containing the thorax displacement value measured when a phase encoding pulse is required,
   (g) determining a specific phase encoding pulse characteristic to be used during the scanning of the subject responsive to the selected interval containing the measured thorax displacement at the time for use of the phase encoding pulse,
   (h) decreasing the number of intervals by increasing the length of the intervals,
   (i) assigning at least one unused phase encoding pulse characteristic to each of the decreased number of intervals to increase the probability of selecting an unused phase encoding pulse with a different characteristic, each assigned phase encoding pulse characteristic determining a different phase,
   (j) repeating the steps of:
      (i) determining a specific phase encoding pulse characteristic,
      (ii) decreasing the number of intervals, and
      (iii) assigning at least one unused phase encoding pulse characteristics to the decreased number of intervals until the scanning is completed.

2. The method of claim 1 wherein the characteristics are amplitudes.

3. The method of claim 2 including using a look-up table for determining a specific phase encoding pulse characteristic responsive to the interval selected and wherein the steps of decreasing the number of intervals and assigning at least one unused phase encoding pulse amplitude to each of the decreased number of intervals comprises changing the look-up table.

4. The method of claim 2 wherein the step of determining the average respiration cycle of the subject to be scanned is accomplished during a learning period.

5. The method of claim 4 wherein the step of determining the average respiration cycle of the subject to be scanned includes constructing a position histogram of the thorax displacement of the subject through a number of respiration cycles.

6. The method of claim 5 wherein the step of assigning at least one phase encoding pulse amplitude to each of the intervals comprises constructing a first look-up table by assigning encoding pulse amplitudes to each of the intervals.

7. The method of reducing respiratory motion artifacts of claim 6 including the steps of,
   inputting the interval selected into the first look-up table generated during the learning period,
   wherein the determining step further comprises using an output of the first look-up table to determine the specific encoding pulse amplitude for immediate use,
   energizing an encoding pulse generator to provide an encoding pulse gradient as a function of the selected encoding pulse amplitude,
   inserting the determined encoding pulse amplitude into a used encoding pulse amplitude inventory, and
   inputting unused encoding pulse amplitudes into a look-up table generator for generating a new look-up table after a given number of encoding pulses are in the used encoding pulse inventory.

8. The method of claim 7 wherein the step of assigning at least one phase encoding pulse amplitude comprises using an analytic mapping function for assigning respiration cycle intervals to encoding pulse amplitudes where the analytic function is based on an approximation to the respiratory cycle.

9. The method of claim 8 wherein the approximation to the respiratory cycle is a sinusoidal function.

10. The method of claim 1 wherein said intervals are intervals of signed thoracic displacement during respiration where the sign is assigned according to the direction of motion.

11. A system for reducing respiratory motion artifacts in nuclear magnetic resonance (NMR) images, said system comprising:
(a) NMR means for scanning a subject,
(b) sensor means for measuring thorax displacement during respiration cycles of the subject,
(c) means for determining the average respiration cycle of the subject based on the measurement of the thorax displacement during a plurality of respiration cycles,
(d) means for dividing the average respiration cycle into a number of intervals,
(e) means for assigning encoding pulse characteristics to each of the intervals,
(f) said sensor means measuring the thorax displacement in the respiration cycle when an encoding pulse is required by the NMR means during a scan of the subject,
(g) means for selecting the present interval of the average respiration cycle that includes the measured thorax displacement in the respiration cycle of the subject when the encoding pulse is required,
(h) means for determining a specific encoding pulse characteristic to be used during the scan of the subject according to the selected interval at the time the encoding pulse is required said specific encoding pulse characteristic defining a specific phase,
(i) said means for determining the encoding pulse characteristic comprises a look-up table comprising intervals corresponding to encoding pulse characteristics, and
(j) means for decreasing the number of intervals by increasing the displacement range of the intervals in the look-up table and for assigning unused encoding pulse characteristics to the decreased number of intervals to increase the probability of having an unused encoding pulse characteristic in each selected interval.

12. The system of claim 11 wherein the characteristics are amplitudes.

13. The method of claim 11 wherein the means for determining the average respiration cycle of the subject to be scanned comprises means for generating a thorax position histogram showing the frequency of each measured thorax displacement after a number of respiration cycles.

14. The system for reducing respiratory motion artifacts of claim 11 wherein the encoding pulse characteristic is the encoding pulse amplitude and wherein the means for selecting the encoding pulse amplitude comprises:
means for inputting the interval selected into a first look-up table generated during a learning cycle,
means responsive to the inputting of the interval selected into the first look-up table for selecting the phase encoding pulse amplitude,
means for providing an encoding pulse gradient as a function of the selected encoding pulse amplitude,
means for placing the selected encoding pulse amplitude into a used encoding pulse inventory, and
means for inputting unused encoding pulse amplitudes into a new look-up table after a given number of encoding pulse amplitudes are in the encoding pulse inventory.

* * * * *